United States Patent
Hindelang et al.

(10) Patent No.: US 10,618,815 B2
(45) Date of Patent: Apr. 14, 2020

(54) PROCESS FOR PRODUCING ORGANICALLY MODIFIED AEROGELS

(71) Applicant: Wacker Chemie AG, Munich (DE)

(72) Inventors: Konrad Hindelang, Munich (DE); Torsten Gottschalk-Gaudig, Mehring (DE); Dominik Jantke, Eching (DE); Richard Weidner, Burghausen (DE)

(73) Assignee: Wacker Chemie AG, Munich (DE)

( * ) Notice: Subject to any disclaimer, the term of this patent is extended or adjusted under 35 U.S.C. 154(b) by 286 days.

(21) Appl. No.: 15/564,317

(22) PCT Filed: Apr. 21, 2016

(86) PCT No.: PCT/EP2016/058833
§ 371 (c)(1),
(2) Date: Oct. 4, 2017

(87) PCT Pub. No.: WO2016/173911
PCT Pub. Date: Nov. 3, 2016

(65) Prior Publication Data
US 2018/0134565 A1      May 17, 2018

(30) Foreign Application Priority Data
Apr. 29, 2015 (DE) .......... 10 2015 207 939

(51) Int. Cl.
*C01B 33/158* (2006.01)
*C01B 33/155* (2006.01)
(Continued)

(52) U.S. Cl.
CPC ....... *C01B 33/1585* (2013.01); *B01J 13/0065* (2013.01); *B01J 13/0069* (2013.01);
(Continued)

(58) Field of Classification Search
CPC ... C01B 33/1585; C01B 33/14; C01B 33/146; B01J 13/0091
(Continued)

(56) References Cited

U.S. PATENT DOCUMENTS 2,945,817 A   7/1960   Goldblum
5,789,495 A   8/1998   Burns et al.
(Continued)

FOREIGN PATENT DOCUMENTS

CA   2274911 A1   6/1998
CN   101691227 B   10/2011
(Continued)

OTHER PUBLICATIONS

English language abstract for CN 101691227 B (2011).
(Continued)

*Primary Examiner* — Michael A Salvitti
(74) *Attorney, Agent, or Firm* — Caesar Rivise, PC (57) ABSTRACT

It is an object of the invention to provide an economically viable process for the production of hydrophobized aerogels which works both inexpensively and in a resource-conserving manner. 2.2. This object is achieved by the provision of a process for producing organically modified aerogels by producing a sol containing [$SiO_{4/2}$] units and [$R_xSiO_{(4-x)/2}$] a units, where x may be the same or different and is 1, 2 or 3, and R may be the same or different and is hydrogen or an organic substituted or unsubstituted radical, using the sol to form a gel, surface-modifying the gel obtained in the presence of more than 0.1% by weight of a phase modifier in a mixture comprising organosiloxane and initiator, wherein the mixture contains at least 20% by weight of organosiloxane and wherein the initiator consists of acid or organosiloxane or mixtures thereof and the gels obtained are dried.

(Continued)

2.3. The aerogels provided can be used as insulating materials, especially in thermal insulation.

20 Claims, 1 Drawing Sheet (51) Int. Cl.
*C01B 33/152* (2006.01)
*B01J 13/00* (2006.01)
*C01B 33/154* (2006.01)
*C07F 7/18* (2006.01)
*C07C 31/08* (2006.01)

(52) U.S. Cl.
CPC ......... *B01J 13/0091* (2013.01); *C01B 33/152* (2013.01); *C01B 33/154* (2013.01); *C01B 33/155* (2013.01); *C01P 2006/10* (2013.01); *C01P 2006/12* (2013.01); *C07C 31/08* (2013.01); *C07F 7/1804* (2013.01)

(58) Field of Classification Search
USPC .......................................... 423/338; 516/100
See application file for complete search history.

(56) References Cited

U.S. PATENT DOCUMENTS

| | | | |
|---|---|---|---|
| 6,481,649 B1 | 11/2002 | Schmidt | |
| 6,620,355 B1 | 9/2003 | Schmidt | |
| 7,297,718 B2 * | 11/2007 | Schwertfeger | C01B 33/1546 423/338 |
| 7,470,725 B2 * | 12/2008 | Schwertfeger | B01J 13/0091 106/490 |
| 2001/0034375 A1 * | 10/2001 | Schwertfeger | B01J 13/0091 516/98 |
| 2003/0207950 A1 * | 11/2003 | Schwertfeger | C01B 33/1546 516/100 |
| 2006/0281828 A1 | 12/2006 | Nakayama et al. | |
| 2018/0044188 A1 * | 2/2018 | Hindelang | C01B 33/152 |
| 2018/0134565 A1 * | 5/2018 | Hindelang | C01B 33/152 |

FOREIGN PATENT DOCUMENTS

| | | |
|---|---|---|
| CN | 102897779 A | 1/2013 |
| CN | 102897779 B | 8/2014 |
| EP | 0963347 B1 | 4/2002 |
| EP | 0948395 B1 | 1/2006 |
| KR | 20000057273 A | 9/2000 |
| KR | 20100010350 A | 2/2010 |

OTHER PUBLICATIONS

English language abstract for CN 102897779 A (2013).
English language abstract for CN 102897779 B (2014).
Schwertfeger et al. (1998). Hydrophobic waterglass based aerogels without solvent exchange or supercritical drying. Journal of Non-Crystalline Solids, 225, 24-29.
Shao et al. (2013). Superhydrophobic sodium silicate based silica aerogel prepared by ambient pressure drying. Materials Chemistry and Physics, 141(1), 570-575.
International Search Report from corresponding PCT/EP2016/058833 dated Jun. 3, 2016.
Machine Translation for KR 20100010350 A (2010).

* cited by examiner

PROCESS FOR PRODUCING ORGANICALLY MODIFIED AEROGELS

CROSS-REFERENCE TO RELATED APPLICATIONS

This application is a U.S. National Phase Application of PCT/EP2016/058833, filed Apr. 21, 2016, which claims priority from DE 10 2015 207 939.2, filed Apr. 29, 2015, the contents of which applications are incorporated herein by reference in their entireties for all purposes.

BACKGROUND OF THE INVENTION

The invention relates to a process for producing organically modified aerogels by preparing a sol comprising $[SiO_{4/2}]$ units and $[R_xSiO_{(4-x)/2}]$ units, where x is 1, 2 or 3 and may be the same or different and R is hydrogen or a substituted or unsubstituted organic moiety and may be the same or different, forming a gel out of the sol, surface modifying the resultant gel in the presence of above 0.1 wt % of a compatibilizer in a mixture comprising organosiloxane and initiator, wherein the mixture comprises not less than 20 wt % of organosiloxane, and wherein the initiator consists of an acid or a chlorosilane or mixtures thereof, and drying the gels obtained.

Aerogels are highly porous rigid solids in that their volume is up to more than 95% pores. Whereas a lyogel represents a liquid-filled structure, the pores of an aerogel are air filled. In a hydrogel, which represents a special instance of lyogel, the pore liquid is not less than 50% water. Owing to their porous structure, aerogels have a high specific surface area, low pore diameters and a particularly low density. These properties make aerogels ideal materials for applications in thermal insulation.

While there are various species of aerogels, those based on silicate are the most widely used, being of particular technical relevance because of their low flammability.

Aerogels comprise an arborization of particle chains having very many interspaces in the form of open cells. These chains have contact points, ultimately resulting in the picture of a stable, spongelike network.

The process of preparing an aerogel is in principle very simple. A first step comprises preparing a corresponding lyogel and a second step comprises drying, i.e., exchanging the solvent for air.

The drying step, i.e., the step of removing the pore liquid, is that step of the process which is determinative for the quality of aerogels. Destruction of the gel structure has to be avoided in the course of this step. There are in essence two strategies for this:

1) "Supercritical drying", i.e., pressure and temperature conditions above the critical point, can be used to ensure that the gel retains its structure and does not shrink or collapse. Capillary forces and hence destruction of the network are substantially avoided in the supercritical domain. The disadvantage of this method is that some technically burdensome, costly high-pressure technology is required for this process and therefore the process is difficult to realize on a large industrial scale, especially as a continuous process.

2) The same result is attainable by drying at atmospheric pressure provided the pore surface was passivated beforehand by modification (silylation). Hence silylation of the free silanol groups in the gel is a way to substantially avoid the gel structure shrinking irreversibly during drying. Since said modification usually utilizes hydrolysis-sensitive chemicals such as trimethylchlorosilane and hexamethyldisilazane, a solvent exchange is generally carried out first. Solvent exchange involves two or more steps wherein the water-containing pore liquid is replaced by inert organic solvents such as hexane in order to avoid the hydrophobing agent (trimethylchlorosilane for example) reacting with the water of the pore liquid.

In addition to stabilizing the structure in the drying step, surface modification leads to a hydrophobicization of the outside and inside surfaces of aerogels. There are many applications where an adequate hydrophobicity is absolutely essential. Especially the field of building insulation requires insulants to be permanently water-repellent, which is why hydrophobic materials are preferred for such applications.

The high specific surface area of aerogels augurs the use as carrier material and transfer agent in chemistry, for catalysis say, or in medicine. Aerogels are by virtue of their specific surface area further also useful as absorbent or filter materials.

The most striking characteristic of aerogels includes their extraordinarily low thermal conductivity. This high insulating effect is made possible by the special construction of aerogels, especially their extraordinary porous structure (densities below 0.2 $g/cm^3$, mesopore volumes above 3 $cm^3/g$ and pore diameters below 25 nm).

Thermal insulation is an important aspect if energy consumption is to be reduced. Especially the field of building insulation is where conventional, inexpensive insulating materials such as polystyrene, polyurethane and glasswool are increasingly coming up against the limits dictated by their high flammability and/or limited insulating effect.

For the use of aerogels to be competitive, an inexpensive method of production is vital. It is accordingly advantageous to minimize the number of processing steps which have to be carried out and, in particular, to preferentially eschew time-consuming operations such as a multi-step solvent exchange.

EP 0 948 395 B1 accordingly disclosed the development of a method for producing organically modified aerogels wherein a hydrogel is surface modified directly, without first exchanging the aqueous pore liquid for organic solvents. The examples utilize a sodium waterglass solution or silicon tetrachloride as $SiO_2$ source and hexamethyldisiloxane (HMDSO, $(CH_3)_3Si-O-Si(CH_3)_3$), trimethylchlorosilane (TMCS, $(CH_3)_3SiCl$) or trimethylsilanol ($(CH_3)_3SiOH$) for modification. The free OH groups of the hydrogel react therein with the silylating agents to form oxygen-bound trimethylsilyl groups (TMS, $(CH_3)_3SiO_{1/2}$). When the silylation is carried out by reacting some of the water in the pores of the hydrogel with the silylation medium used (e.g., TMCS) to form the water-insoluble hexamethyldisiloxane, the volume of the compound formed will necessarily displace at least some of the water out of the pores. This, during the silylation of the inside surface of the network, leads to a concurrent, complete or partial exchange of liquid in the pores of the hydrogel for the water-insoluble medium.

The method disclosed has the disadvantage that the surface modification (silylation) either takes place at high temperatures of 80-100° C. or requires a very long reaction period of several days. Only the use here of large amounts of HCl and/or trimethylchlorosilane will ensure a rapid and complete form of surface modification. During the hydrophobing step, the pore liquid is displaced out of the gel and replaced by HMDSO, in which connection the authors of this patent, F. Schwertfeger and D. Frank, in a subsequent publication with M. Schmidt in the *Journal of non-Crystal-*

*line Solids* (vol. 225, pp. 24-29, 1998), specify that a complete exchange of the pore liquid requires not less than 15 mol % of TMCS based on the pore water, corresponding to 81.5 g of TMCS per 100 g of hydrogel (see sample 2 in table 1), to obtain a complete exchange of the pore liquid and hence aerogels of low density (below 140 kg/m$^3$). And 80 ml of HMDSO are by-produced per 100 g of hydrogel. So a disposal issue is created in addition to costs being incurred for the raw material. The aqueous HCl partly contaminated with salts is generally unrecyclable, but has to be disposed of via the wastewater. The high excess of trimethylchlorosilane generates a large amount of hexamethyldisiloxane, which needs an additional processing step to convert back into trimethylchlorosilane. Similarly, the reaction heat generated by the use of large amounts of TMCS requires an increased engineering effort on the process design side. For that reason, but also in order to minimize the amount of hazardous substances and thereby increase processing safety, the amount of hydrochloric acid and trimethylchlorosilane should be minimized.

The authors of the patents CN 101691227 and CN 102897779 likewise carry out a surface modification of the lyogel in order to be able to do away with supercritical drying and hence reduce manufacturing costs, and also to provide a simple process for producing silicated aerogels. In contradistinction to EP 0 948 395 B1 and the cited publication by Schwertfeger, Frank and Schmidt, CN 101691227 and CN 10897779 utilize silicated gels already "premodified" by cocondensation of methyltrimethoxysilane (MTMS) or methyltriethoxysilane (MTES) with SiO$_2$ sources such as waterglass or TEOS and, following a solvent exchange, surface modify the resultant silicated lyogels in a second step with a solution of TMCS in hexane. However, the solvent exchange and the dilution of the silylating agent in hexane lead to very long reaction times, which compromises implementation on a large industrial scale. The handling of chlorosilanes such as TMCS has the disadvantage that open systems cannot be used at comparatively high temperatures because of the low boiling point of TMCS (57° C.) for example. TMCS is further classified as a flammable, corrosive and toxic substance. Substituting hydrochloric acid for TMCS, as is possible with the use of HMDSO as solvent, is not possible with the use of hexane as solvent. After the reaction, hexane, TMCS and also the HMDSO formed in the course of the reaction of TMCS with the pore water have to be separated off or disposed of, which creates additional costs.

DESCRIPTION OF THE INVENTION

The problem addressed by the invention is therefore that of providing an economical method for producing hydrophobed aerogels that is inexpensive, simple and safe/consistent in handling and does not waste resources.

The problem is solved by providing a process for producing organically modified aerogels by preparing a sol comprising [SiO$_{4/2}$] units and [R$_x$SiO$_{(4-x)/2}$] units, where x is 1, 2 or 3 and may be the same or different and R is hydrogen or a substituted or unsubstituted organic moiety and may be the same or different, forming a gel out of the sol, surface modifying the resultant gel in the presence of above 0.1 wt % of a compatibilizer in a mixture comprising organosiloxane and initiator, wherein the mixture comprises not less than 20 wt % of organosiloxane and wherein the initiator consists of an acid or a chlorosilane or mixtures thereof, and drying the gels obtained.

As already noted in the introduction, aerogels are highly porous rigid solids where the pores are air filled. By contrast, a lyogel is a gel whose pores are solvent filled. The pore liquid of a hydrogel consists to not less than 50% of water.

The first step comprises preparing a sol comprising [SiO$_{4/2}$] units and [R$_x$SiO$_{(4-x)/2}$] units (where x is 1, 2 or 3 and may be the same or different and R is hydrogen or a substituted or unsubstituted organic moiety and may be the same or different). In the present invention, a sol is a solution and/or colloidal dispersion of molecules and/or particles in at least one solvent and/or dispersion medium.

A solvent is a substance which is capable of thinning or dissolving gases, liquids or solids without chemical reactions between solute and solvent occurring in the process.

A dispersion is a heterogeneous mixture of two or more substances that scarcely dissolve in or chemically combine with each or one another, if at all. One or more of these substances (the disperse phase) is in a fine state of subdivision in some other continuous substance (dispersion medium, interchangeably =continuous phase). Disperse phases having a particle size of typically about 1 nm to 1 μm are classified according to their particle size as dissolved in a colloidally disperse manner.

The moieties R may be the same or different and each independently represent hydrogen, an organic, linear, branched, cyclic, saturated or unsaturated, aromatic or heteroaromatic moiety, with or without substituents. This means that the moieties R may be substituted or unsubstituted. Preferred substituents are —CN, —NCO, —NR$_2$, —COOH, —COOR, -halogen, -(meth)acryloyl, -epoxy, —SH, —OH, —CONR$_2$, —O—R, —CO—R, —COO—R, —OCO—R, or —OCOO—R, —S—R, —NR—, —N=R, —N=N—R, or —P=R. Preference is given to using saturated or unsaturated moieties comprising C$_1$-C$_4$-, more preferably C$_1$-C$_4$-alkyl, vinyl, especially methyl or ethyl, specifically methyl.

The [SiO$_{4/2}$] units signify compounds in which a silicon atom is bonded to four oxygen atoms which in turn each have a free electron for a further bond. Units bonded via the oxygen atom and having Si—O—Si bonds may be present. The free oxygen atoms are in the simplest case bonded to hydrogen or carbon, or the compounds are in the form of salts preferably alkali metal salts.

The starting material (precursor) used for forming [SiO$_{4/2}$] units ([SiO$_{4/2}$] starting material) may be condensation-capable tetrafunctional or more highly functional silanes, alkoxysilanes, alkyl silicates, alkali metal silicates or colloidal silica particles/solutions known to a person skilled in the art.

The starting material used for [SiO$_{4/2}$] units preferably comprises compounds of the type Si(OR)$_4$, [SiO$_{4/2}$]$_w$ [SiO$_{3/2}$(OR)]$_x$[SiO$_{2/2}$(OR)$_2$]$_y$[SiO$_{1/2}$(OR)$_3$]$_z$ (where w, x, y, z are each a nonnegative integer), SiCl$_4$, waterglasses or colloidal silica solutions. R in each case is as defined above. It is particularly preferred to use tetraethyl orthosilicate (TEOS) or sodium waterglass. It is also possible to use mixtures or hydrolysis products of the recited starting materials, especially their hydrolysis products with water and/or alcohols.

Waterglass refers to glassy, i.e., amorphous, water-soluble sodium, potassium and lithium silicates solidified from a melt, or aqueous solutions thereof. Neutralizing the salt and hydrolysis converts the catenary Si—O—Si compounds into [SiO$_{4/2}$] units.

Particular preference is given to using tetraethyl orthosilicate (TEOS). The hydrolysis of TEOS in water may be catalyzed by acids or bases:

$$C_8H_{20}O_4Si + 4H_2O \rightarrow H_4SiO_4 + 4C_2H_5OH$$

where the resultant orthosilicic acid ($H_4SiO_4$) crosslinks further by formation of Si—O—Si bonds and loss of water until stoichiometrically silicon dioxide is formed:

$$H_4SiO_4 \rightarrow H_2SiO_3 + H_2O$$

$$H_2SiO_3 \rightarrow SiO_2 + H_2O$$

The hydrolysis of tetraalkoxysilanes is preferably carried out in aqueous solutions of mineral or organic acids, more preferably in aqueous hydrochloric acid solution.

In the $[R_xSiO_{(4-x)/2}]$ units (where x=1, 2 or 3 and may be the same or different), not only one, two or three oxygen atoms but additionally one, two or three moieties R are bonded directly to the silicon atom. R is as defined hereinabove. The $[R_xSiO_{(4-x)/2}]$ units may all have bonded to the silicon atom either one moiety R and three oxygen atoms, i.e., x=1, or two moieties R and two oxygen atoms, i.e., x=2, or three moieties R and one oxygen atom, i.e., x=3. There may also be mixtures comprising $[RSiO_{3/2}]$ units and/or $[R_2SiO_{2/2}]$ units and/or $[RSiO_{1/2}]$ units. Again $O_{(4-x)/2}$ (e.g., $O_{3/2}$, $O_{2/2}$ or $O_{1/2}$) represents (4-x) (=3, 2 or 1) oxygen atoms which each have a free electron for a further bond.

The Si—R groups of the $[R_xSiO_{(4-x)/2}]$ unit provide the product (i.e., the gel) with a basic hydrophobicization.

The starting material (precursor) used for forming $[R_xSiO_{(4-x)/2}]$ units ($[R_xSiO_{(4-x)/2}]$ starting material) may be condensation-capable bifunctional, trifunctional or more highly functional silanes, alkoxysilanes or siliconates which are known to a person skilled in the art. It is optionally also possible to use monofunctional silanes, alkoxysilanes or siliconates. R is as defined above.

Preference is given to using compounds of the type $RSi(OR)_3$, $RSiCl_3$, $[RSi(OH)_{3-n}(OM)_n]$ (where n is a non-negative integer between 0 and 3 and M=Li, Na, K) and also their hydrolysis and/or condensation products, $[RSiO_{3/2}]_x[RSiO_{2/2}(OR)]_y[RSiO_{1/2}(OR)_2]_z$ (where x, y and z are each a non-negative integer), $R_2Si(OR)_2$, $R_2SiCl_2$, $[R_2Si(OH)_{2-m}(OM)_m]$ (where m is a non-negative integer between 0 and 2, and M=Li, Na, K) and their hydrolysis and/or condensation products, $[R_2SiO_{2/2}]_y[R_2SiO_{1/2}(OR)]_z$ (where y and z are each a non-negative integer), $R_3SiCl$, $R_3SiOR$, $R_3Si$—$O$—$SiR_3$, $R_3Si$—$NH$—$SiR_3$, $R_3SiOH$, $R_3SiOM$ (where M=Li, Na, K). R is as defined above.

Particular preference is given to using methyltrialkoxysilanes, vinyltrialkoxysilanes, dimethyldialkoxysilanes, OH—, OR—, H— or Cl-terminated polydimethylsiloxanes, alkali metal methylsiliconates.

The starting material used for the $[R_xSiO_{(4-x)/2}]$ units is methyltriethoxysilane (MTES), methyltrimethoxysilane, potassium methylsiliconate or sodium methylsiliconate with particular preference. It is also possible to use mixtures, hydrolysis products and/or condensation products of the recited starting materials, especially their hydrolysis products with water and/or alcohols. Methyltriethoxysilane (MTES) is used with particular preference.

The starting materials for $[SiO_{4/2}]$ and $[R_xSiO_{(4-x)/2}]$ units and optionally also added-substance and auxiliary materials are used to prepare a sol by methods known to the notional person skilled in the art. Sol preparation is to be understood as meaning the step of mixing starting materials with at least one solvent/dispersant. This mixing step may also be accompanied and/or followed by a reaction of the starting material.

Sols of alkoxysilanes are for example prepared by hydrolysis to liberate the corresponding alcohols. The hydrolysis can be accelerated by admixture of an acid and/or temperature increase. Sols from waterglasses and/or siliconates are prepared, for example, by neutralizing the strong basic alkali metal silicates and/or alkylsiliconates. This may be accomplished by methods known to a person skilled in the art, as described in EP 0 948 395 B for example, by neutralization with mineral acids and using acidic ion exchange resins.

The sol may additionally have added to it added substances such as IR opacifiers known to a person skilled in the art, to reduce the thermal conductivity. Similarly, to increase the mechanical stability, coated and/or uncoated fibers may be added. Useful fiber materials include inorganic fibers, for example glass fibers or mineral fibers, organic fibers, for example polyester fibers, aramid fibers, nylon fibers or fibers of vegetable origin, and also mixtures thereof.

To prepare mixed sols, i.e. sols comprising $[SiO_{4/2}]$ units and $[R_xSiO_{(4-x)/2}]$ units, the starting materials are mixed according to the prior art and a sol is prepared according to the methods described above. Mixing the starting materials at the same time leads to cocondensation of the various units. By contrast, a time-shifted, preferably later admixture of some or all the $[R_xSiO_{(4-x)/2}]$ starting materials into the still liquid sol provides a concentration change for the $[R_xSiO_{(4-x)/2}]$ units in the primary particles from in to out. The concentration of $[R_xSiO_{(4-x)/2}]$ units preferably increases in the primary particles from in to out. The later admixture of some of the $[R_xSiO_{(4-x)/2}]$ starting materials will provide for an accumulation of the $[R_xSiO_{(4-x)/2}]$ units on the surface of the sol particles and hence a gradient-type or core-shell construction and thus achieve a maximal basic hydrophobicization for a minimal proportion of $[R_xSiO_{(4-x)/2}]$ units. In a gradient-type construction, the concentration of $[R_xSiO_{(4-x)/2}]$ units increases gradually, i.e., nonabruptly, from in to out. In a core-shell construction, the concentration of $[R_xSiO_{(4-x)/2}]$ units, by contrast, increases abruptly from in to out.

The concentration of $[R_xSiO_{(4-x)/2}]$ units is preferably below 20 mol %, more preferably below 10 mol % and yet more preferably 0 mol % in the core and preferably above 80 mol %, more preferably above 90 mol % and yet more preferably 100 mol % in the shell.

It is advantageous in this connection for the initially charged starting materials for $[SiO_{4/2}]$ units and for some or all of the $[R_xSiO_{(4-x)/2}]$ units to have already been substantially converted into the sol before the admixture of the remaining or as the case may be all starting materials for $[R_xSiO_{(4-x)/2}]$ units. Thorough conversion is obtainable through a temperature increase and/or delay time. Later time-shifted admixture into the still liquid sol is to be understood in the context of this invention as meaning that the admixture of the first starting materials is followed by a period of preferably 5 minutes to 10 hours, more preferably 30 minutes to 5 hours and yet more preferably 30 min to 2 hours of incubation under continued agitation before the remaining starting materials for $[R_xSiO_{(4-x)/2}]$ are admixed. The liquid sol at this stage is preferably temperature-regulated to a temperature between 5 and 100° C., more preferably between 10 and 80° C. and yet more preferably between 15 and 40° C.

In a preferred embodiment of the process, therefore, the step of preparing the sol (step i) is carried out by admixing not less than 1 wt %, more preferably not less than 25 wt %, yet more preferably not less than 50 wt % and yet even more preferably not less than 80 wt %, of the starting materials to form $[R_xSiO_{(4-x)/2}]$ ($[R_xSiO_{(4-x)/2}]$ starting materials) units to the already initially charged starting materials. A particularly preferred embodiment comprises admixing the entire portion of the $[R_xSiO_{(4-x)/2}]$ starting materials to the sol later. It is thus possible to prepare first a sol just of the $[SiO_{4/2}]$ starting materials or a sol of $[SiO_{4/2}]$ starting materials and a portion of the $[R_xSiO_{(4-x)/2}]$ starting materials and to admix the remaining portion of the $[R_xSiO_{(4-x)/2}]$ starting materials into the still liquid sol before/during or after the start of gel formation. The proportion of $[R_xSiO_{(4-x)/2}]$ units (based on the sum total of $[SiO_{4/2}]$ units and $[R_xSiO_{(4-x)/2}]$ units) is preferably in the range between 1 and 80 mol %, more preferably between 1 and 60 mol % and yet more preferably between 5 and 50 mol %. The solids content of the sol, i.e., its concentration of $[SiO_{4/2}]$ units and $[R_xSiO_{(4-x)/2}]$ units, is generally between 3 and 30 wt %, preferably between 5 and 20 wt % and more preferably between 8 and 15 wt %.

A preferred embodiment uses tetraethoxysilane (TEOS) as $[SiO_{4/2}]$ starting material and methyltriethoxysilane (MTES) as $[R_xSiO_{(4-x)/2}]$ starting material. The two starting materials are initially mixed and under agitation in water converted using hydrochloric acid as catalyst. The solvent or solvent mixture used for sol preparation comprises, in general, water or homogeneous mixtures of water and polar organic solvents, preferably alcohols. The water content here is preferably high enough for the water-containing mixture to form a separate liquid phase in the silylation medium. As mentioned, the admixture of the $[R_xSiO_{(4-x)/2}]$ precursor may also be time shifted in order to obtain an accumulation of the hydrophobic $[R_xSiO_{(4-x)/2}]$ units on the surface of the primary particles and eventually also on the surface of the gel, and/or to completely cover the surface of the primary particles and of the gel with $[R_xSiO_{(4-x)/2}]$ units. Sol formation can be accelerated by admixture of catalysts, preferably acids. Mineral acids or organic acids are usable. The use of hydrochloric acid is particularly preferred. The hydrochloric acid here serves as catalyst for the hydrolysis of the alkoxy groups. The HCl concentration here is preferably 10-1000 ppm, preferably 30-300 ppm, more preferably 100-200 ppm. The reaction mixture may be heated to hasten the hydrolysis. This step proceeds with preference at 40 to 80° C., with particular preference at 55-65° C. for a period of preferably 0.1 to 3 hours, more preferably 0.5 to 1 hour. The result is the formation of a clear sol which may optionally also be stored for several hours to days. But preferably the sol is further reacted directly.

Comparable sols are also obtainable on the basis of waterglass, especially sodium waterglass as $[SiO_{4/2}]$ precursor and alkali metal methylsiliconate, especially sodium or potassium methylsiliconate and/or methyltrialkoxysilane as $[R_xSiO_{(4-x)/2}]$ precursor via methods known to the notional person skilled in the art (e.g. EP 0 948 395 B or Example 6). Neutralizing the precursors and removing the salts generated in the process may be effected by any method known to the notional person skilled in the art (ion exchanger, precipitation in the form of spearing soluble salts, washing off, etc.).

The 2nd step of the process, step (ii), comprises forming a gel out of the sol. Gel formation is effected by methods known to a person skilled in the art such as pH increase and/or temperature increase. The gel-forming step may be followed by an aging step, which is can also be accelerated by known methods such as pH control and heating.

To initiate gel formation, the sol is preferably admixed with a base, and rendered weakly alkaline, under agitation. A gel formation pH established for the gel-forming step in the alkoxysilane-based process is preferably in the range from 7 to 10 and more preferably between 8.5 and 9.5. Any of the bases known to a person skilled in the art such as $NH_4OH$, $NaOH$, $KOH$, $Al(OH)_3$, silicates or siliconates are generally usable for this purpose, preference being given to the use of $NH_4OH$ (ammonia), waterglass or alkali metal methylsiliconate. Hastening of the gel formation time is also achievable via a temperature increase. The temperature at which the gel-forming step is carried out is generally between 0° C. and the boiling point of the solvents present, preferably between 40° C. and 80° C. and more preferably between 50 and 70° C.

Sols based on waterglass as $[SiO_{4/2}]$ precursor are preferably converted into a gel at a pH between 3 and 10, more preferably between 4 and 7 and at a temperature between the freezing point and the boiling point of the solvents present, preferably between 0 and 60° C., especially between 0 and 30° C., specifically between 5 and 20° C.

The gel obtained may subsequently be subjected to an aging step. An aging step for the purposes of the invention comprises carrying out the gel at a temperature in the range from 20 to 100° C., preferably 50 to 70° C. and more preferably at 60° C. for 1 second to 48 hours, preferably 30 min to 24 hours and more preferably 30 min to 3 hours and a pH of 4-11, preferably 7-10 and more preferably 8-9.

The 3rd step of the process, step (iii), comprises surface modifying the resultant gel in the presence of above 0.1 wt % of a compatibilizer in a mixture comprising organosiloxane and initiator, wherein the mixture comprises not less than 20 wt % of organosiloxane, and wherein the initiator consists of an acid or a chlorosilane or mixtures thereof.

A compatibilizer as the term is understood in the present application comprehends a polar compound or mixtures of various such compounds that has a marked solubility not only in the water-rich phase but also in the organic phase and thus hastens the mass transfer between the two essentially immiscible phases.

The surface-modifying step of the present invention takes place in the presence of above 0.1 wt % of a compatibilizer. A suitable compatibilizer comprises polar organic compounds or mixtures thereof such as

- alcohols, especially of the chemical formula R—OH, where R is as defined above for moieties R (e.g., methanol, ethanol, isopropanol)
- ketones, especially of the chemical formula $R^1R^2C$=O, where $R^1$ and $R^2$ are the same or different and are each as defined above for moieties R (e.g., acetone $(CH_3)_2C$=O)
- ethers, especially of the chemical formula $R^1OR^2$, where $R^1$ and $R^2$ are the same or different and are each as defined above for moieties R (e.g., diethyl ether, tetrahydrofuran, dimethoxyethane)
- esters, especially of the chemical formula $R^1COOR^2$, where $R^1$ and $R^2$ are the same or different and are each as defined above for moieties R (e.g., ethyl acetate), and
- surface-active substances such as surfactants. Surface-active is applied to organic compounds which by virtue of their structure locate at the interface between two phases such that they lower the interface tension (=surface tension) and thereby enable, for example, wetting. By lowering the surface tension, they further the commixing of two phases possibly up to the formation of an emulsion. Depending on their chemical composition and use, surface-active substances are designated as wetting agents, detergents (surfactants, soap) or emulsifiers.

The substances in question each comprise in general one hydrophilic ("water-friendly") group, which strongly attracts water, and one lipophilic ("fat-friendly") hydrocarbonaceous group which attracts water molecules but weakly (and so is in fact hydrophobic).

The compatibilizer used more preferably comprises alcohols such as, for example, methanol, ethanol and isopropanol, while it is particularly preferable to use ethanol as compatibilizer.

The compatibilizer may not only be imported into the sol/gel through a reaction of the precursors (hydrolysis) but also be admixed directly to the sol/gel or into the organosiloxane phase (even combinations are possible). In a preferred embodiment, the compatibilizer is admixed in the step of preparing the sol or is formed therefrom. This means that compatibilizer is present in the sol immediately the sol is formed (step i). The compatibilizer may be formed for example out of the hydrolysis of methyltriethoxysilane (MTES), tetraethoxysilane (TEOS) or dimethyldimethoxysilane (DMDMS).

A silylation medium is to be understood in the present application as meaning organosiloxanes, especially disiloxanes, and also solutions thereof in nonreactive polar solvents, while the silylation medium may optionally comprise initiators such as chlorosilanes, especially trimethylchlorosilane, acids, especially hydrochloric acid (HCl), and also scission products forming out of the organosiloxane, especially disiloxane. The solvents are preferably hydrocarbons such as pentane, hexane, heptane and toluene.

By organosiloxanes there are meant in the present application linear, cyclic or branched compounds of the type $[R_3SiO_{1/2}]_m[R_2SiO]_n[RSiO_{3/2}]_o[SiO_2]_p$ (where m, n, o, p are each an integer$\geq 0$), where R is as defined above. A linear organosiloxane has for example the general formula $R_3Si$—$[O$—$SiR_2]_n$—$O$—$SiR_3$. The rule is that an organosiloxane has at least one Si—C bond, i.e., at least one moiety has to be organic in nature.

Mixtures of various organosiloxanes, preferably liquid organosiloxanes are also usable according to the invention. A disiloxane is preferably used as organosiloxane.

Disiloxanes are chemical compounds having the formula $R_3Si$—$O$—$SiR_3$ or $[R^1R^2R^3SiO_{1/2}]_2$, where again R, $R^1$, $R^2$ and $R^3$ are each as defined above and the disiloxane has at least one Si—C bond. Preference is given to using symmetrical disiloxanes, more preferably hexamethyldisiloxane. It is also possible to use mixtures of various disiloxanes, especially mixtures of hexamethyldisiloxane and divinyltetramethyldisiloxane. In the surface-modifying step, the free and accessible silanol groups of the silicative lyogel react with the silylation medium. In a preferred embodiment, Si—O—SiR$_3$ groups are formed out of Si—OH groups in the course of this reaction.

The silylation media needed for the actual silylating reaction may also be generated from other substances, preferably other silylation media, for example in the manner of reactions and mechanisms known to a person skilled in the art (*Journal of non-Crystalline Solids* (vol. 225, pp. 24-29, 1998), EP 0 948 395 B), e.g., by scissioning the organosiloxane in an acidic medium, especially by scissioning of HMDSO in hydrochloric acid.

The proportion of organosiloxane, preferably disiloxane, in the silylation medium for the purposes of the invention is not less than 20 wt %, preferably not less than 50 wt %, more preferably not less than 90 wt % and yet more preferably not less than 95 wt %. In a yet still more preferable embodiment, the proportion of organosiloxane in the mixture is not less than 98 wt %, i.e., commercially available concentrated organosiloxane, preferably disiloxane, more preferably hexamethyldisiloxane is used.

Before, during or after any aging step, the (lyo)gel formed may be washed with water, polar organic solvents or mixtures thereof in order to remove electrolytes for example. The lyogel may also be washed without an aging step being carried out. It is advantageous for the subsequent process for the pore liquid to contain sufficient water to be able to form a separate phase in the silylation medium. It is therefore particularly preferable to do completely without a solvent exchange and/or washing step in order, for example, to minimize the processing costs and time, i.e., for step iii to take place without solvent exchange beforehand.

The lyogel formed may be mixed with the silylation medium before, during or after an optionally performed aging step, preferably during or after the optionally performed aging step. The amount of silylation medium used per ml of lyogel is preferably not less than 1 ml, more preferably 1-4 ml and yet more preferably 1-2 ml of silylation medium.

Before, during or after the step of admixing the silylation medium or before the step of transferring the lyogel into the silylation medium, it is preferable for the gel to be comminuted. This has the advantage of resulting in good commixing, a large proportion for contact areas of the gel with the silylation medium and hence rapid subsequent processes, especially a rapid rate of surface modification. The gel is for this forced through a sieve having the desired mesh size. In general, however, comminution may be effected by any method known to the notional person skilled in the art, such as dispersing, grinding, chaffing, cutting.

An alternative preferred embodiment eschews comminuting the ready-produced pieces of gel by effecting shaping before and/or simultaneously with gel formation in step ii. In a particularly preferred embodiment, shaping is effected concurrently with the step of gel formation.

In a particularly preferred embodiment, the liquid sol prepared according to any one of the embodiments described is transferred into the silylation medium. The admixture of the sol is accompanied and/or followed by a step of shaping the sol droplets and/or the resultant particles of gel by methods known to a person skilled in the art (emulsifying, dispersing, spraying for example), preferably by dispersing, more preferably by emulsifying. Dispersing is to be understood as meaning that the liquid sol is distributed, by stirring, in a continuous phase (the dispersion medium) and therein the sol droplets are converted into gel droplets.

It is particularly preferred for the continuous phase to also be the silylation medium. This means that, in this preferred embodiment, shaping is effected by dispersing the sol in a continuous phase, while the continuous phase comprises not less than 20 wt %, preferably not less than 50 wt %, more preferably not less than 90 wt % and yet more preferably not less than 95 wt % of organosiloxane. That is, the continuous phase also serves as reagent for surface modification.

Gel formation may be initiated as described under step ii above, before, during or after the admixture of the sol into the silylation medium, according to the above-described methods, such as raising the pH and/or the temperature. When a base is used to start gel formation, this base may be introduced into the sol and/or into the continuous phase.

This preferred embodiment provides a distinct improvement for the overall process over the prior art because the reaction processes, especially that of surface modification, are hastened by virtue of the smaller size of the gel particles and the good commixing. Emulsions/dispersions are further much simpler to convey, particle sizes are simple to control, and no additional comminuting step is needed for the gels. This simplifies any large-scale industrial manufacture because a continuous or semi-continuous process is made possible as a result. In a specifically preferred embodiment, the continuous phase used is a technically pure organosiloxane, preferably hexamethyldisiloxane. This is particularly advantageous because, as a result, no burdensome separation and workup of mixtures is required and the organosiloxane, preferably hexamethyldisiloxane, is directly reusable after the reaction.

On admixture with a base under agitation, the sol converts, again under agitation, into the organosiloxane within a minute (see Invention Examples 1-3). The gel formation period may extend from a few seconds up to several hours, depending on the pH and the temperature. It is advantageous to adjust the length of the gel formation period such that the sol is still liquid at the time of admixture to the silylation medium, so the sol is still conveyable in a simple manner and shaping is possible in a controlled manner. Advantageously, the base is only admixed directly before the step of dispersing the sol, by means of suitable mixing apparatuses known to a person skilled in the art, especially those having short residence times such as static mixers. The base may also already be included in the continuous phase. The step of admixing a base may also be dispensed with in the case of a temperature-induced form of gel formation. It is advantageous in this case to heat the continuous phase. The step of dispersing the sol may be carried out in apparatuses known to a person skilled in the art (examples being stirred tanks and tubular reactors). The shape and size of the gel particles which form in the process is controllable via parameters such as stirrer speed, stirrer and/or reactor geometry and the ratio between the sol and the silylation medium. The ratio of continuous phase/sol (the volume of the continuous phase/the volume of the sol) is generally above 1, preferably between 1 and 10, more preferably between 1 and 4, yet more preferably between 1 and 2. Preferred conditions for gel formation and aging were already described in the preceding, preferred embodiment (as described above under step ii).

The (lyo)gel formed may have separated from it, before, during or after any aging step being carried out, a portion of the continuous phase (by filtration, decantation, centrifugation, evaporation for example) in order, for example, to increase the concentration of gel particles in the dispersion and thus, for example, increase space-time yields in the subsequent steps.

Before, during or after any aging step, the (lyo)gel formed may be washed with water, polar organic solvents or mixtures thereof in order to remove electrolytes for example.

The gels obtained in the embodiments described are subjected to a surface-modifying step, this surface-modifying step being carried out after any optionally performed aging step. The reaction conditions prevailing in the gel-forming step and aging step mean that, in general, no or but very slow surface modification takes place in the silylation medium because the organosiloxanes, especially disiloxanes, are but very slow to silylate under these conditions, if they do so at all. Organosiloxanes, preferably disiloxanes, can be precisely initiated by admixture of acids or acid donors such as chlorosilanes. The term "initiator" in this invention is thus an acid or a chlorosilane, or mixtures thereof, and hastens the rate of surface modification. This enables a better form of process control. This is a significant advantage for the process of the invention over the most commonly used prior art mixture of hydrocarbons and trimethylchlorosilane. It is part of the invention for the surface-modifying step to be initiated by admixture of acids and/or chlorosilanes through the already described reactions and mechanisms known to a person skilled in the art. It is particularly preferred to use hydrochloric acid or trimethylchlorosilane (TMSC) or their mixtures as initiator. It is especially preferable to use concentrated hydrochloric acid. The TMCS in effect acts as silylation medium, reacts with the silanol groups on the gel surface and thereby leads to substantial hydrophobicization of the structure. When hydrochloric acid is used as initiator, the active silylating agent first has to form out of the organosiloxane, preferably disiloxane, and hydrochloric acid (by scissioning of disiloxane for example), which in Example 5 b and Comparative Examples 1b and 2b leads to a markedly delayed start to surface modification. This delay, however, can be shortened by intensive mixing. It is accordingly advantageous to carry out the surface-modifying step in emulsion. The active silylating agent may also undergo a secondary reaction with the water of the pore liquid to form the corresponding organosiloxane, preferably disiloxane. It is accordingly advantageous to conduct the surface-modifying step in organosiloxanes, preferably disiloxanes, and/or in a very concentrated organosiloxane solution, since this serves to maintain a sufficiently high concentration of active silylation medium due to the above-described retroreaction with acid. Moreover, the avoidance of a further solvent, such as hexane, makes possible a simple and hence economical form of material recovery, since the aqueous phase and the organosiloxane, preferably disiloxane, phase need merely be separated. This can be done by the methods for separating organic and aqueous phases that are known to a person skilled in the art (e.g., settling pond, centrifuge, decanter, distillation, . . . ). A particularly preferred embodiment therefore utilizes a mixture of organosiloxane, preferably disiloxane, and initiator as silylation medium and eschews admixing a further solvent.

During hydrophobicization, the polar, water-containing pore liquid is displaced out of the gel and replaced by the organosiloxane and/or the organosiloxane-rich organic phase, preferably disiloxane, more preferably by HMDSO. Since the aqueous pore liquid is substantially immiscible with the organosiloxane-rich phase, a second, aqueous, liquid phase forms during the surface-modifying step. Since the aqueous phase preferably has a higher density than the organosiloxane-rich phase and the gel particles preferentially reside in the organic phase, the method of the invention provides a simple and resource-sparing form of a separation process. This is of particular importance for large-scale industrial practice in particular. What is more, the progress of the reaction can be tracked via the amount of displaced pore liquid. The volume of displaced pore liquid is read off on a scale in Example 5 and Comparative Examples 1-4 in order to glean meaningful information about the rate of the silylation reaction.

Since polar liquids, especially water, are held in purely $[SiO_{4/2}]$ gels by very strong bonds due to the high hydrophilicity and the low pore diameters of the network and the compatibility/miscibility between water and HMDSO is very low, the abovementioned method due to Schwertfeger (EP 0 948 395 B1) is reliant on high processing temperatures and/or high amounts of HCl and/or TMCS. Surprisingly, the incorporation of $[R_xSiO_{(4-x)/2}]$ units in combination with the use of compatibilizers enables the surface modification of lyogels in organosiloxane or organosiloxane solutions to be carried out at lower temperatures and with distinctly smaller amounts of initiators such as HCl and TMCS in industrially sensible times of a few hours.

It is part of the invention that the time for the process of surface modification and solvent displacement is preferably less than 12 hours, more preferably between 15 minutes and 3 hours, yet more preferably between 15 minutes and 2 hours and most preferably between 15 and 60 minutes. The silylation reaction can be carried out below or above the boiling points of the substances involved. If desired, the reaction may also be carried out under superatmospheric pressure for example to be able to achieve higher reaction temperatures. The surface-modifying step is preferably carried out between room temperature and the boiling point of the silylation medium and/or the pore liquid. The temperature at which the reaction is carried out is preferably between 50 and 90° C., more preferably between 60 and 80° C. The compatibilizer may be present in the sol and/or in the silylation medium. The compatibilizer can be admixed to the silylation medium and/or the gel and/or the sol before the surface-modifying step. The compatibilizer is preferably already present in the sol. The compatibilizer may in effect be admixed to the sol before, during or after the preparation thereof. More preferably, the compatibilizer is formed from the $[SiO_{4/2}]$ precursor and/or the $[R_xSiO_{(4-x)/2}]$ precursor during sol preparation. The compatibilizer used more preferably comprises ethanol and/or methanol formed out of the hydrolysis of the precursors. The compatibilizer content of the pore liquid in the present invention is above 0.1 wt %, preferably between 0.1 and 90 wt %, more preferably between 1 and 50 wt % and yet more preferably between 5 and 30 wt %.

To minimize the processing costs, it is advantageous to minimize the use of acid and/or chlorosilane. The amount of initiator used per 100 g of gel is preferably not more than 20 g, more preferably not more than 10 g and yet more preferably not more than 5 g. To ensure good commixing and hence a rapid rate of mass transfer, the surface-modifying step is advantageously carried out under agitation. It therefore represents a particularly preferred embodiment to carry out the surface-modifying step in a dispersion (Examples 1-3).

Figure 1:
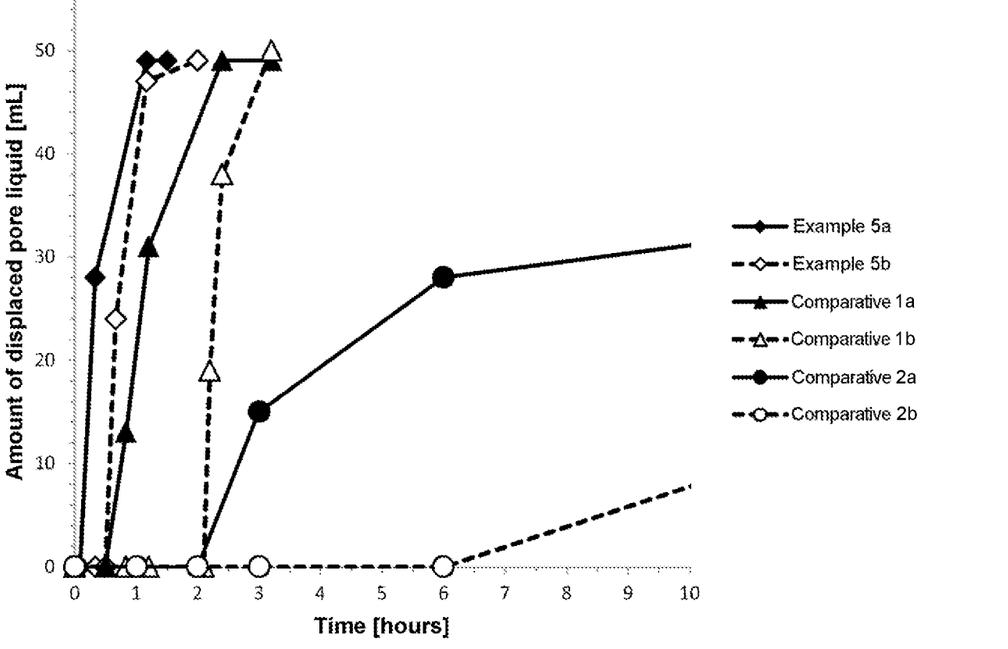
FIG. 1 is a graph of the amount of displaced pore liquid against time.

The examples (Example 5a versus 5b, Comparative Example 1a versus 1b and 2a versus 2b, see FIG. 1) show that the hydrophobicization is startable with TMCS as well as HCl. $[R_xSiO_{(4-x)/2}]$ units used according to the invention in sol preparation is found to hasten the displacement of the aqueous pore liquid in the gel (Example 5a/5b versus 1a/1b and 2a/2b, see FIG. 1). A first pointer to this effect emerged in a paper by Z. Shao, F. Luo, X. Cheng and Y. Zhang (Material Chemistry and Physics 141, pp. 570-575, 2013). The authors write that the solvent exchange of the pore water for ethanol is improved by the hydrophobicization of the network with MTES. Nonetheless, at 48 hours, surface modification by using a silylation medium that is not in accordance with the invention (a mixture of TMCS, ethanol and hexane) is distinctly too slow to develop an economical process therefrom.

Surprisingly, this effect is greatly enhanced, i.e., the reaction rate greatly raised, when at one and the same time ethanol is used as compatibilizer and organosiloxane is used as silylation medium. The use of the $[R_xSiO_{(4-x)/2}]$ units in the manner of the invention and the presence of a compatibilizer serve to greatly hasten the process for producing the organically modified aerogel. Comparative Example 4 shows that the TMCS-hexane mixture does not deliver any marked reaction even after 24 hours on using the low TMCS quantity of the invention and the low reaction temperatures of the invention. Absent basic hydrophobicization (i.e. absent admixture of $[R_xSiO_{(4-x)/2}]$ units) and absent compatibilization (without compatibilizer), no reaction took place with a silylation medium of the invention (Comparative Example 3). The procedure of the invention (Example 5) raised the reaction rate by a factor of not less than 2 versus a procedure without basic hydrophobicization (Example 5a versus Comparative Example 1a). Versus a surface modification without a compatibilizer, the rate was hastened by a factor of not less than 18 (Example 5a: 28 ml in 0.33 h versus Comparative Example 2a: 28 ml in 6 h). The low solids contents of the sol mean that, in general, very high volumes of matter have to be turned over in the manufacture of aerogels. Space-time yield minimization is therefore dispositive for the development of an economical process as well as TMCS quantity minimization. To wit, hastening the surface modification by a factor of 2 can raise the throughput by 100 percent, leading to a significant reduction in processing costs.

It is advantageous to separate the gel particles from the aqueous phase and the excess silylation medium following the surface-modifying step. This is done by filtration in the examples of the invention. The separation process can be carried out via any of the solid-liquid and/or liquid-liquid separation methods known to a person skilled in the art (e.g., decanter, settling pool, centrifuges, water traps, distillation, . . .). The gel or reaction mixture may be washed and/or extracted with solvents before, during or after the separating step. It is particularly advantageous to wash the reaction mixture with water in order to remove the electrolytes.

The next step of the method according to the invention comprises drying the surface-modified and optionally washed gel. The gel is dried to constant weight in a vacuum drying cabinet at 0.01 bar and 80° C. in the Invention Example. In general, the drying step may be carried out not only in the supercritical domain but also in the subcritical domain. Drying preferably takes place below the critical point, preferably at temperatures of −30 to 200° C., more preferably 0 to 150° C., and also at pressures preferably of 0.001 to 20 bar, more preferably 0.01 to 5 bar, especially 0.01 to 2 bar. This drying step may be effected by radiative, convective and/or contact drying. Drying is preferably carried on until the gel has a residual solvent content of less than 0.1 wt %.

The drying step may optionally be preceded, accompanied or followed, preferably accompanied or followed, by a step of agglomerating the gels into larger particles. This may for example be effected by known methods (see for instance U.S. Pat. Nos. 6,481,649 B1 and 6,620,355 B1).

The present invention therefore makes available a process for producing organically modified aerogels that is inexpensive, simple, safe/consistent in handling and resource sparing and thus economical. The process of the invention is particularly notable for combining the advantages of a rapid course of reaction and of using low quantities of initiator with mild conditions for the temperature. The particularly preferred embodiment, gel preparation and surface modification in dispersion, makes available a process which by virtue of a particularly efficient form of material recovery, rapid form of mass transfer and rapid reaction steps makes possible the realization of a continuous large-scale industrial process. The individual advantages were already detailed above.

Aerogels obtainable by the process of the invention are hydrophobic. The molar fraction of $[R_xSiO_{(4-x)/2}]$ units in the aerogel is preferably in the range from 1 to 99%, more preferably in the range from 5 to 60% and yet more preferably in the range from 5 to 50%. The density of said aerogels is preferably in the range from 0.05 to 0.3 g/cm$^3$, more preferably in the range from 0.08 to 0.2 g/cm$^3$ and yet more preferably in the range of 0.09 and 0.15 g/cm$^3$. The surface area of said aerogels, as determined via the BET method, is preferably in the range between 300 and 1000 m$^2$/g, more preferably between 500 and 900 m$^2$/g, especially between 600 and 800 m$^2$/g. The aerogels obtained according to the invention are notable for a BJH pore volume of preferably not less than 2.0 cm$^3$/g, more preferably not less than 3 cm$^3$/g, yet more preferably not less than 4.0 cm$^3$/g. The aerogels obtained according to the invention possess a low level of thermal conductivity. The latter when measured at 20° C. is preferably less than 0.02 W/mK, more preferably less than 0.015 W/mK and especially less than 0.01 W/mK.

The organically modified aerogels obtainable according to the invention are thus used with preference for insulation applications, more preferably in thermal and/or acoustic insulation and yet more preferably as thermal insulant.

The invention will now be more particularly described with reference to exemplary embodiments without being limited thereby.

Analytical Methods:

Determination of Bulk Density

Bulk density was determined according to DIN 53468 by pouring the aerogel powder without further compaction into a cylindrical vessel of known volume (50 cm$^3$) and then determining the weight of the aerogel powder by weighing.

Determination of Mass Density

Pycnometry was used to determine the mass density of the aerogel pieces. The aerogel pieces were weighed on an analytical balance (m$_1$) and the water displacement in a 25 ml pycnometer (DIN ISO 3507 Gay-Lussac glass pycnometer from Blaubrand) was measured at room temperature for volume determination. The following masses were determined on an analytical balance:

m$_2$: Mass of pycnometer filled with distilled water
m$_3$: Mass of pycnometer filled with the aerogel piece and distilled water The volume of the aerogel piece (V$_1$) corresponds to the volume of the displaced water (V$_2$). The volume and the mass density of the aerogel piece were computed according to the following formulae:

$$V_1 = V_2 = \rho_w * (m_2 - (m_3 - m_1))$$

$$\rho_{Aerogel} = m_1/V_1$$

where $\rho_w$ is the mass density of water at room temperature (0.998 g/cm$^3$).

Care was taken when filling the pycnometer with the aerogel piece and the water not to entrap any air bubbles. The high hydrophobicity of the aerogel samples prevents any ingress of water into the pores of the samples. As a check, the weight of the aerogel pieces was confirmed after the measurement by renewed weighing.

Determination of BET Surface Area

Specific surface area was determined for the aerogels by the BET method of DIN 9277/66131 and 9277/66132.

Determination of BJH Pore Volume and of Median Pore Diameter

Pore analysis was carried out by the method of Barett Joyner and Halenda (BJH, 1951) in accordance with DIN 66134. Desorption isotherm data were evaluated.

Determination of Yield

To determine the yield, the gel particles were dried to constant weight and then weighed at room temperature.

Determination of Thermal Conductivity

Thermal conductivity was determined using a THB Transient Hot Bridge Analyzer (THB-100) from Linseis by using a THB Hot Point Sensor (3×3 mm Kapton) at room temperature (measurement time 100 seconds, current strength: 5 mA, heating power: 2 mW). The size of the aerogel pieces measured was about 10×10 mm.

Determination of pH pH was determined using a pH meter from Mettler Toledo Seven Multi; electrode: In Lab Science.

EXAMPLES

Suppliers applicable to all examples:
Tetraethyl orthosilicate (WACKER® TES28 from Wacker Chemie AG), methyltriethoxysilane (SEMICOSIL® M3E from Wacker Chemie AG), dimethyldimethoxysilane (Sigma-Aldrich, Grade: 95%), waterglass (Sigma-Aldrich: SiO$_2$ content: 26.5 wt %, Na$_2$O content: 10.6 wt %), potassium methylsiliconate (SILRES® BS 16 from Wacker Chemie AG), hexamethyldisiloxane (WACKER® AK 0.65 SILICONOEL from Wacker Chemie AG), trimethylchlorosilane (SILAN M3 from Wacker Chemie AG).
All other laboratory chemicals were obtained from Sigma-Aldrich, unless otherwise mentioned.
Aerogel production in emulsions (Examples 1-3), unless otherwise stated, utilized a KPG stirrer in the stirred steps at a speed of 400 revolutions per minute (rpm).

Example 1

A round-bottom flask was initially charged with 675 ml of water and 3.3 ml of 1 M hydrochloric acid before heating to 60° C. Under intensive stirring, a mixture formed from 156 g of TEOS and 134 g of MTES was admixed and stirred at 60° C. for 2 hours. The molar ratio of TEOS:MTES was 1:1.

In a second flask, 2000 ml of hexamethyldisiloxane were intensively stirred.

The warm sol was intensively stirred while being admixed with 40 ml of 0.25 M ammonia solution and transferred within a minute into the second round-bottom flask holding the HMDSO.

The reaction mixture was stirred for 1 hour at room temperature and then for 2 hours at 60° C. Gel formation and aging took place during this period. Then, 100 g of concentrated hydrochloric acid were admixed with stirring and the reaction mixture was stirred at 60° C. for 60 minutes during which an aqueous phase was formed.

The gel particles were subsequently separated off by filtration using a Büchner funnel (Whatman® Filter, 125 mm, Grade 40).

The gel particles were finally dried in a vacuum drying cabinet (10 mbar, 80° C.). The following values were determined as described in the analytical methods:
bulk density: 0.11 g/cm$^3$
BET: 750 m$^2$/g
BJH pore volume: 4.0 cm$^3$/g
median pore diameter: 22 nm
yield: 117.3 g Example 2

A round-bottom flask was initially charged with 675 ml of water and 3.3 ml of 1 M hydrochloric acid before heating to 60° C. Under intensive stirring, a mixture formed from 226 g of TEOS and 64 g of MTES was admixed and stirred at 60° C. for 2 hours. The molar ratio of TEOS:MTES was 3:1.

In a second flask, 2000 ml of hexamethyldisiloxane were intensively stirred.

The warm sol was intensively stirred while being admixed with 36 ml of 0.25 M ammonia solution and transferred within a minute into the second round-bottom flask holding the HMDSO. The reaction mixture was stirred for 1 hour at room temperature and then for 2 hours at 60° C. Gel formation and aging took place during this period. Then, 100 g of concentrated hydrochloric acid were admixed with stirring and the reaction mixture was stirred at 60° C. for a further 2 hours, during which an aqueous phase was formed as a result of the hydrophobicization and the associated solvent exchange.

The gel particles were subsequently separated off by filtration using a Büchner funnel (Whatman® Filter, 125 mm, Grade 40).

The gel particles were finally dried in a vacuum drying cabinet (10 mbar, 80° C.). The following values were determined as described in the analytical methods:
bulk density: 0.14 g/cm$^3$
BET: 850 m$^2$/g
BJH pore volume: 4.2 cm$^3$/g
median pore diameter: 15 nm
yield: 108.7 g

Example 3

A round-bottom flask was initially charged with 650 ml of water and 3 ml of 1 M hydrochloric acid before heating to 60° C. Under intensive stirring, a mixture formed from 271 g of TEOS and 26 g of MTES was admixed and stirred at 60° C. for 1.5 hours. The molar ratio of TEOS:MTES was 9:1.

In a second flask, 1500 ml of hexamethyldisiloxane were heated to 60° C. and intensively stirred.

The warm sol was intensively stirred while being admixed with 37 ml of 0.25 M ammonia solution and transferred within a minute into the second round-bottom flask holding the HMDSO. The reaction mixture was stirred at 60° C. for 3 hours. Then, 100 g of concentrated hydrochloric acid were admixed with stirring and the reaction mixture was stirred at 60° C. for a further 2 hours, during which an aqueous phase was formed as a result of the hydrophobicization and the associated solvent exchange. The gel particles were subsequently separated off by filtration using a Büchner funnel (Whatman® Filter, 125 mm, Grade 40). The gel particles were finally dried in a vacuum drying cabinet (10 mbar, 80° C.). The following values were determined as described in the analytical methods:
bulk density: 0.12 g/cm$^3$
BET: 840 m$^2$/g
BJH pore volume: 4.2 cm$^3$/g
median pore diameter: 16 nm
yield: 113 g

Example 4

A round-bottom flask was initially charged with 449 g of water and 0.7 ml of 1 M hydrochloric acid before heating to 60° C. Under intensive stirring, a mixture formed from 104 g of TEOS and 89 g of MTES was admixed and stirred at 60° C. for 2 hours. The molar ratio of TEOS:MTES was 1:1.

After cooling down to room temperature, the sol was mixed in a glass beaker with 25 ml of 0.25 M ammonia solution. For aging, the gel obtained was incubated in a sealed vessel in a drying cabinet at 60° C. for 3 hours. The gel was subsequently divided into pieces about 10 mm in size. 50 g of the gel pieces were overlayered with 100 ml of HMDSO and, at 50° C., admixed with 5.0 g of TMCS and incubated in a sealed screw top flask for 2 hours at 50° C. in a drying cabinet. Then, the gel pieces were separated off by filtration via a Büfunnel (Whatman® Filter, 125 mm, Grade 40) and dried to constant weight in a vacuum drying cabinet (80° C. and 10 mbar). Run 1 and Run 2 represent two independent replications of Example 4. The following values were determined as described in the analytical methods:
Run 1:
Mass density: 0.12 g/cm$^3$
BET surface area: 795 m$^2$/g
BJH pore volume: 4.23 cm$^3$/g
Median pore diameter: 22.4 nm
Thermal conductivity: 0.011 W/m*K
Run 2:
Mass density: 0.11 g/cm$^3$
BET surface area: 804 m$^2$/g
BJH pore volume: 3.97 cm$^3$/g
Median pore diameter: 18.2 nm
Thermal conductivity: 0.01 W/m*K Thermal conductivity has the unit of watt per meter per kelvin (W/m*K).

Example 5

Determination of Hydrophobicization and Solvent Exchange Rates in Gels With Basic Hydrophobicization and Presence of Compatibilizer A round-bottom flask was initially charged with 449 g of water and 0.7 ml of 1 M aqueous hydrochloric acid and heated to 60° C. Under intensive stirring, a mixture formed from 104 g of TEOS and 89 g of MTES was admixed and stirred at 60° C. for 2 hours. After cooling down to room temperature, the sol was admixed in a glass beaker with 25 ml of 0.25 M ammonia solution. The gel obtained was subsequently aged, i.e. incubated in a sealed vessel for 3 hours at 60° C. in a drying cabinet. Subsequently, the gel was pressed through a sieve having a mesh size of 5 mm in order to obtain pieces below 5 mm in size. The gel pieces were subsequently reacted as per versions a), b) and c).
a) In a sealed screw top flask, 50 g of gel and 100 ml of HMDSO at 50° C. were admixed with 5.0 g of trimethylchlorosilane, shaken and the amount of the aqueous phase displaced out of the gel was read off on a scale. The results are listed in Table 1. It transpired that the hydrophobicization, displacing the aqueous pore liquid, was complete after one hour.
b) In a sealed screw top flask, 50 g of gel and 100 ml of HMDSO at 50° C. were admixed with 5.0 g of concentrated hydrochloric acid, shaken and the amount of the aqueous phase displaced out of the gel was read off on a scale. The results are listed in Table 1. It transpired that the hydrophobicization, displacing the aqueous pore liquid, was complete after one hour.
c) In a sealed screw top flask, 50 g of gel and 100 ml of an HMDSO solution (50 wt % in n-hexane) at 50° C. were admixed with 5.0 g of trimethylchlorosilane, shaken and the amount of the aqueous phase displaced out of the gel was read off on a scale. It transpired that the hydrophobicization, displacing the aqueous pore liquid, was complete after two hours.

Example 6

In a glass beaker, 150.0 g of water, 75.0 g of waterglass and 75.0 g of potassium methylsiliconate were mixed and cooled to 10° C. in an ice bath.

In a screw top flask, 200 g of hydrochloric acid (7.5 wt %) were initially charged, cooled to below 10° C. in an ice bath and stirred at 500 rpm with a magnetic stirrer.

The cooled waterglass-potassium methylsiliconate solution was gradually added via a dropping funnel to the hydrochloric acid solution with stirring. Care was taken with the metered addition to ensure that the temperature does not rise above 10° C. At pH 5.3 the admixture was stopped and the reaction mixture heated to room temperature, resulting in gel formation taking place. For aging, the gel obtained was incubated in a sealed vessel in a drying cabinet at 60° C. for 3 hours.

Subsequently, the gel was pressed through a sieve having a mesh size of 5 mm in order to obtain pieces below 5 mm in size. To remove the salts, the gel pieces were incubated in hot water (300 ml of water per 100 g of gel) at 60° C. three times for 12 hours at a time. The incubating water was decanted off after 12 hours in each period, to then be replaced by fresh water. Before the surface-modifying step, 100 g of the moist gel were overlayered with 200 ml of an ethanol-water mixture (50 wt % ethanol) and incubated in a sealed vessel at room temperature for 16 hours. The gel was subsequently separated off by filtration using a Büfunnel (Whatman® Filter, 125 mm, Grade 40). For surface modification, the gel pieces obtained were admixed, shaken and incubated in a drying cabinet at 60° C. for 4 hours with 200 ml of HMDSO and 10.0 g of trimethylchlorosilane in a sealed screw top flask. The gel pieces were subsequently separated off by filtration using a Büfunnel (Whatman® Filter, 125 mm, Grade 40) and dried to constant weight under reduced pressure in a vacuum drying cabinet (10 mbar, 120° C.). The following values were determined as described in the analytical methods:
mass density: 0.11 g/cm$^3$
BET: 511 m$^2$/g Example 7

In a glass beaker, 108.8 g of water and 108.8 g of waterglass were mixed and cooled to 10° C. in an ice bath. In a second glass beaker, 11.6 g of water and 11.6 g of potassium methylsiliconate were mixed and cooled to 10° C. in an ice bath. In a screw top flask, 200 g of hydrochloric acid (7.5 wt %) were initially charged, cooled to below 10° C. in an ice bath and stirred at 500 rpm with a magnetic stirrer.

The cooled waterglass solution was gradually added via a dropping funnel to the hydrochloric acid solution with stirring. Care was taken with the metered addition to ensure that the temperature does not rise above 10° C. After admixture, the reaction mixture was stirred at room temperature for two hours and cooled back down to below 10° C. before admixing the second component. Then, the cooled potassium methylsiliconate solution was gradually added via a dropping funnel with stirring, care being taken with the metered addition to ensure that the temperature does not rise above 10° C. Then, the stirrer was removed and the sol warmed to room temperature, resulting in gel formation taking place.

For aging, the gel obtained was incubated in a sealed vessel in a drying cabinet at 60° C. for 3 hours. Thereafter, the gel was pressed through a sieve having a mesh size of 5 mm in order to obtain pieces below 5 mm in size. To remove the salts, the gel pieces were incubated in hot water (300 ml of water per 100 g of gel) at 60° C. three times for 12 hours at a time. The incubating water was decanted off after 12 hours in each period, to then be replaced by fresh water.

Before the surface-modifying step, 100 g of the moist gel were overlayered with 200 ml of an ethanol-water mixture (50 wt % ethanol) and incubated in a sealed vessel at room temperature for 16 hours. The gel was subsequently separated off by filtration using a Büfunnel (Whatman® Filter, 125 mm, Grade 40). For surface modification, the gel pieces obtained were admixed, shaken and incubated in a drying cabinet at 60° C. for 2 hours with 200 ml of HMDSO and 10.0 g of trimethylchlorosilane in a sealed screw top flask. The gel pieces were subsequently separated off by filtration using a Büfunnel (Whatman® Filter, 125 mm, Grade 40) and dried to constant weight under reduced pressure in a vacuum drying cabinet (10 mbar, 120° C.). The following values were determined as described in the analytical methods:
mass density: 0.11 g/cm$^3$
BET: 498 m$^2$/g
BJH pore volume: 3.25 cm$^3$/g
median pore diameter: 22.1 nm Example 8

In a screw top flask, 84 g of water and 0.2 ml of aqueous hydrochloric acid 1 M were initially charged and heated to 60° C. Under intensive agitation (magnetic stirrer, 500 rpm), a mixture of 41.2 g of TEOS and 2.40 g of dimethyldimethoxysilane (DMDMS) was admixed and stirred at 60° C. for 2 hours. The molar ratio of TEOS:DMDMS was 9:1. The sol was subsequently admixed with 5 ml of 0.25 M ammonia solution. For aging, the gel obtained was incubated in a sealed vessel in a drying cabinet at 60° C. for 3 hours. The gel was subsequently divided into pieces about 10 mm in size. 50 g of the gel pieces were overlayered with 100 ml of HMDSO and, at 50° C., admixed with 5.0 g of TMCS and incubated in a sealed screw top flask for 2 hours at 50° C. in a drying cabinet. Then, the gel pieces were separated off by filtration via a Büfunnel (Whatman® Filter, 125 mm, Grade 40) and dried to constant weight in a vacuum drying cabinet (80° C. and 10 mbar). The following values were determined as described in the analytical methods:
mass density: 0.17 g/cm$^3$
BET surface area: 790 m$^2$/g Comparative Example 1

Determination of hydrophobicization and solvent exchange rates without basic hydrophobicization of the gel, in the presence of a compatibilizer In a round-bottom flask, 451 g of water and 0.7 ml of 1 M aqueous hydrochloric acid were initially charged and heated to 60° C. Under intensive agitation, 208 g of TEOS were admixed and stirred at 50° C. for 2 hours. After cooling down to room temperature, the sol was admixed in a glass beaker with 25 ml of 0.25 M ammonia solution. For aging, the gel obtained was incubated in a sealed vessel in a drying cabinet at 60° C. for 3 hours. Subsequently, the gel was pressed through a sieve having a mesh size of 5 mm in order to obtain pieces below 5 mm in size. The gel pieces were subsequently reacted according to versions a) and b).

a) In a sealed screw top flask, 50 g of gel and 100 ml of HMDSO at 50° C. were admixed with 5.0 g of trimethylchlorosilane, shaken and the amount of the aqueous phase displaced out of the gel was read off on a scale. The results are listed in Table 1. It transpired that the hydrophobicization, displacing the aqueous pore liquid, was complete after two hours.

b) In a sealed screw top flask, 50 g of gel and 100 ml of HMDSO at 50° C. were admixed with 5.0 g of concentrated hydrochloric acid, shaken and the amount of the aqueous phase displaced out of the gel was read off on a scale. The results are listed in Table 1. It transpired that the hydrophobicization, displacing the aqueous pore liquid, was complete after three hours.

Comparative Example 2

Determination of hydrophobicization and solvent exchange rates with basic hydrophobicization of the gel, in the absence of a compatibilizer The gel pieces below 5 mm were prepared as described under Example 5.

Instead of silylation according to versions a), b) or c), the gel pieces were incubated in hot distilled water (300 ml of water per 100 g of gel) at 60° C. five times for 24 hours at a time to remove the ethanol. The incubating water was decanted off after 24 hours in each period, to then be replaced by fresh water. The gel pieces were subsequently reacted according to versions a) and b).
a) In a sealed screw top flask, 50 g of gel and 100 ml of HMDSO at 50° C. were admixed with 5.0 g of trimethylchlorosilane, shaken and the amount of the aqueous phase displaced out of the gel was read off on a scale. The results are listed in Table 1. It transpired that 24 hours later 85% by volume of the pore liquid quantity to be expected had been displaced out of the gel.
b) In a sealed screw top flask, 50 g of gel and 100 ml of HMDSO at 50° C. were admixed with 5.0 g of concentrated hydrochloric acid, shaken and the amount of the aqueous phase displaced out of the gel was read off on a scale. The results are listed in Table 1. It transpired that 24 hours later 70% by volume of the pore liquid quantity to be expected had been displaced out of the gel.

Comparative Example 3

Determination of hydrophobicization and solvent exchange rates without basic hydrophobicization of the gel, in the absence of a compatibilizer The gel pieces below 5 mm were prepared as described under Comparative Example 1.

Instead of silylation according to versions a), b) or c), the gel pieces were incubated in distilled water (300 ml of water per 100 g of gel) at 60° C. five times for 24 hours at a time to remove the ethanol. The incubating water was decanted off after 24 hours in each period, to then be replaced by fresh water. The gel pieces were subsequently reacted according to versions a) and b).
a) In a sealed screw top flask, 50 g of gel and 100 ml of HMDSO at 50° C. were admixed with 5.0 g of trimethylchlorosilane, shaken and the amount of the aqueous phase displaced out of the gel was read off on a scale. Over a period of 24 hours no reaction took place in the form of pore liquid displacement.
b) In a sealed screw top flask, 50 g of gel and 100 ml of HMDSO at 50° C. were admixed with 5.0 g of concentrated hydrochloric acid, shaken and the amount of the aqueous phase displaced out of the gel was read off on a scale. Over a period of 24 hours no reaction took place in the form of pore liquid displacement.

Comparative Example 4

Determination of hydrophobicization and solvent exchange rates for same amount of trimethylchlorosilane as in example 5a and comparative examples 1a, 2a and 3a by substitution of n-hexane for hexamethyldisiloxane
a) In a sealed screw top flask, 50 g of aged and comminuted gel obtained as described in Example 5 and 100 ml of n-hexane were, at 50° C., admixed and shaken with 5.0 g of trimethylchlorosilane and the amount of the aqueous phase displaced out of the gel was read off on a scale. Over a period of 24 hours no reaction took place in the form of pore liquid displacement.
b) In a sealed screw top flask, 50 g of aged and comminuted gel obtained as described in Comparative Example 2 and 100 ml of n-hexane were, at 50° C., admixed and shaken with 5.0 g of trimethylchlorosilane and the amount of the aqueous phase displaced out of the gel was read off on a scale. Over a period of 24 hours no reaction took place in the form of pore liquid displacement.
b) In a sealed screw top flask, 50 g of washed gel obtained as described in Comparative Example 2 and 100 ml of n-hexane were, at 50° C., admixed and shaken with 5.0 g of trimethylchlorosilane and the amount of the aqueous phase displaced out of the gel was read off on a scale. Over a period of 24 hours no reaction took place in the form of pore liquid displacement.
d) In a sealed screw top flask, 50 g of washed gel obtained as described in Comparative Example 3 and 100 ml of n-hexane were, at 50° C., admixed and shaken with 5.0 g of trimethylchlorosilane and the amount of the aqueous phase displaced out of the gel was read off on a scale. Over a period of 24 hours no reaction took place in the form of pore liquid displacement.

Example 9

In a glass beaker, 80.0 g of waterglass and 65.0 g of water were mixed and cooled to 10° C. in an ice bath. In a screw top flask, 100 g of hydrochloric acid (7.5 wt %) were initially charged, cooled to below 10° C. in an ice bath and stirred at 500 rpm with a magnetic stirrer.

The cooled waterglass solution was gradually added via a dropping funnel to the hydrochloric acid solution with stirring. Care was taken with the metered addition that the temperature does not rise above 15° C. The addition was stopped at pH 2.5. Then, under agitation, 6.25 g of MTES were admixed and the mixture removed from the ice bath. Once the sol was clear, 40.0 g of ethanol were admixed. Lastly, 0.25 M ammonia solution was admixed to establish pH 5.5, resulting in gel formation taking place. For aging, the gel obtained was incubated in a sealed vessel in a drying cabinet at 60° C. for 3 hours. Subsequently, the gel was pressed through a sieve having a mesh size of 5 mm, to obtain pieces below 5 mm.

For surface modification, 100 g of the gel pieces obtained were admixed, shaken and incubated with 200 ml of HMDSO and 10.0 g of hydrochloric acid (32% strength) in a sealed screw top flask at 70° C. in a drying cabinet for 4 hours during which the reaction vessel was shaken every 15 min or so. The gel pieces were subsequently separated off by filtration, washed with water and dried to constant weight at reduced pressure in a vacuum drying cabinet (10 mbar, 120° C.). The following values were determined as described in the analytical methods:
bulk density: 0.09 g/cm$^3$
BET: 790 m$^2$/g Example 10

In a glass beaker, 82.0 g of waterglass, 5.0 g of potassium methylsiliconate and 50.0 g of water were mixed and cooled to 10° C.

In a screw top flask, 100 g of hydrochloric acid (7.5 wt %) were initially charged, cooled to below 10° C. in an ice bath and stirred at 500 rpm with a magnetic stirrer.

The cooled waterglass-potassium methylsiliconate solution was gradually added via a dropping funnel to the hydrochloric acid solution with stirring. Care was taken with the metered addition that the temperature does not rise above 15° C. The addition was stopped at pH 1.5. Then, under agitation, 100.0 g of the compatibilizer were admixed (85 g of ethanol (a), 100 g of methanol (b), 100 g of isopropanol (c)) and the mixture was removed from the ice bath. Lastly, 0.25 M ammonia solution was admixed to establish pH 5.5, resulting in gel formation taking place. For aging, the gel obtained was incubated in a sealed vessel in a drying cabinet at 60° C. for 3 hours. Subsequently, the gel was pressed through a sieve having a mesh size of 5 mm, to obtain pieces below 5 mm.

For surface modification, 100 g of the gel pieces obtained were admixed, shaken and incubated with 200 ml of HMDSO, 10.0 g of hydrochloric acid (32% strength) and in a sealed screw top flask at 70° C. in a drying cabinet for 4 hours during which the reaction vessel was shaken every 15 min or so. The gel pieces were subsequently separated off by filtration, washed with water and dried to constant weight at reduced pressure in a vacuum drying cabinet (10 mbar, 120° C.). The following values were determined as described in the analytical methods:

a) Bulk density: 0.09 g/cm$^3$
b) Bulk density: 0.06 g/cm$^3$
c) Bulk density: 0.06 g/cm$^3$ Example 11

In a glass beaker, 115 g of water and 1.5 g of 1 M aqueous hydrochloric acid were initially charged. Under agitation, a mixture formed from 47.5 g of TEOS and 1.4 g of trimethylethoxysilane was admixed and stirred at room temperature for 16 hours.

For gel formation, the sol was admixed with 5.0 g of 0.5 M ammonia solution. For aging, the gel obtained was incubated in a sealed vessel in a drying cabinet at 60° C. for 4 hours. The gel was subsequently divided into pieces about 5 mm in size. For surface modification, 100 g of the gel pieces obtained were admixed, shaken and incubated with 200 ml of HMDSO, 10.0 g of hydrochloric acid (32% strength) and 10 g of ethanol in a sealed screw top flask at 70° C. in a drying cabinet for 3 hours during which the reaction vessel was shaken every 15 min or so. The gel pieces were subsequently separated off by filtration, washed with water and dried to constant weight at reduced pressure in a vacuum drying cabinet (10 mbar, 120° C.). The following values were determined as described in the analytical methods:

bulk density: 0.11 g/cm$^3$
BET: 715 m$^2$/g

TABLE 1

| Time | Amount of displaced pore liquid [ml] | | | | | |
|---|---|---|---|---|---|---|
| | Example | | Comparative Example | | | |
| [h] | 5a | 5b | 1a | 1b | 2a | 2b |
| 0.00 | 0.00 | 0.00 | 0.00 | 0.00 | 0.00 | 0.00 |
| 0.08 | 0.00 | 0.00 | nd | nd | nd | nd |
| 0.33 | 28.00 | 0.00 | nd | nd | nd | nd |
| 0.50 | nd | 0.00 | 0.00 | nd | nd | nd |
| 0.67 | nd | 24.00 | nd | nd | nd | nd |
| 0.83 | nd | nd | 13.00 | 0.00 | nd | nd |
| 1.00 | nd | nd | nd | nd | 0.00 | 0.00 |
| 1.17 | 49.00 | 47.00 | nd | nd | nd | nd |
| 1.20 | nd | nd | 31.00 | 0.00 | nd | nd |
| 1.50 | 49.00 | nd | nd | nd | nd | nd |
| 2.00 | nd | 49.00 | nd | nd | 0.00 | 0.00 |
| 2.10 | nd | nd | nd | 0.00 | nd | nd |
| 2.20 | nd | nd | nd | 19.00 | nd | nd |
| 2.40 | nd | nd | 49.00 | 38.00 | nd | nd |
| 3.00 | nd | nd | nd | nd | 15.00 | 0.00 |
| 3.20 | nd | nd | 49.00 | 50.00 | nd | nd |
| 6.00 | nd | nd | nd | nd | 28.00 | 0.00 |
| 24.00 | nd | nd | nd | nd | 42.00 | 35.00 | nd = not determined

The invention claimed is:

1. A process for producing organically modified aerogels, said process comprising:
   i) preparing a sol comprising SiO$_{4/2}$ units and R$_x$SiO$_{(4-x)/2}$ units, wherein a compatibilizer is admixed in the step of preparing the sol or is formed out of the sol,
   ii) forming a gel out of the sol, wherein the compatibilizer constitutes 1 to 50 wt % of a pore liquid,
   iii) surface modifying the gel in a presence of more than 0.1 wt % of a compatibilizer in a mixture comprising an organosiloxane and an initiator, wherein the mixture comprises not less than 20 wt % of the organosiloxane, and wherein the initiator consists of an acid or a chlorosilane or mixtures thereof,
   iv) and drying the gels obtained,
   wherein each x is 1, 2 or 3 and may be the same or different and
   wherein each R is hydrogen or a substituted or unsubstituted organic moiety and may be the same or different.

2. The process as claimed in claim 1, wherein the step of preparing the sol (step i) is carried out by admixing not less than 1 wt % of starting materials to form R$_x$SiO$_{(4-x)/2}$ units to already initially charged starting materials.

3. The process as claimed in claim 1, wherein step iii takes place without a solvent exchange occurring before step iii.

4. The process as claimed in claim 1, wherein the initiator consists of trimethylchlorosilane or hydrochloric acid or mixtures thereof.

5. The process as claimed in claim 1, wherein shaping is effected concurrently with the step of gel formation.

6. The process as claimed in claim 1, wherein the organosiloxane used is hexamethyldisiloxane.

7. The process as claimed in claim 5, wherein said shaping is effected by dispersing the sol in a continuous phase, wherein the continuous phase comprises not less than 20 wt % of the organosiloxane and simultaneously serves as a reagent for surface modification.

8. The process as claimed in claim 1, wherein alcohols are used as the compatibilizer.

9. The process as claimed in claim 8, wherein ethanol is used as the compatibilizer.

10. The process as claimed in claim 1, wherein not more than 20 g of the initiator are used per 100 g of the gel.

11. The process as claimed in claim 1, wherein SiO$_{4/2}$ starting material used is tetraethoxysilane (TEOS) and a $R_xSiO_{(4-x)/2}$ starting material used is methyltriethoxysilane (MTES) or hydrolysis products thereof.

12. The process as claimed in claim 2, wherein step iii takes place without a solvent exchange beforehand.

13. The process as claimed in claim 12, wherein the initiator consists of trimethylchlorosilane or hydrochloric acid or mixtures thereof.

14. The process as claimed in claim 13, wherein shaping is effected concurrently with the step of gel formation.

15. The process as claimed in claim 14, wherein the organosiloxane used is hexamethyldisiloxane.

16. The process as claimed in claim 15, wherein said shaping is effected by dispersing the sol in a continuous phase, wherein the continuous phase comprises not less than 20 wt % of the organosiloxane and simultaneously serves as a reagent for surface modification.

17. The process as claimed in claim 16, wherein alcohols are used as the compatibilizer.

18. The process as claimed in claim 17, wherein ethanol is used as the compatibilizer.

19. The process as claimed in claim 18, wherein not more than 20 g of the initiator are used per 100 g of the gel.

20. The process as claimed in claim 19, wherein a $SiO_{4/2}$ starting material used is tetraethoxysilane (TEOS) and a $R_xSiO_{(4-x)/2}$ starting material used is methyltriethoxysilane (MTES) or hydrolysis products thereof.

\* \* \* \* \*